United States Patent
Chen et al.

(10) Patent No.: US 10,809,207 B2
(45) Date of Patent: Oct. 20, 2020

(54) RAY CALIBRATION DEVICE AND OPERATING METHOD THEREOF, AND RADIATION IMAGING SYSTEM AND OPERATING METHOD THEREOF

(71) Applicant: NUCTECH COMPANY LIMITED, Beijing (CN)

(72) Inventors: Zhiqiang Chen, Beijing (CN); Yumei Chen, Beijing (CN); Yaohong Liu, Beijing (CN); Xinshui Yan, Beijing (CN); Weiqiang Guan, Beijing (CN); Wei Yin, Beijing (CN)

( * ) Notice: Subject to any disclaimer, the term of this patent is extended or adjusted under 35 U.S.C. 154(b) by 352 days.

(21) Appl. No.: 15/281,038

(22) Filed: Sep. 29, 2016

(65) Prior Publication Data
US 2017/0184513 A1    Jun. 29, 2017

(30) Foreign Application Priority Data
Dec. 28, 2015 (CN) .......................... 2015 1 1000945

(51) Int. Cl.
*G01N 23/04* (2018.01)
*G01T 7/00* (2006.01)
(Continued)

(52) U.S. Cl.
CPC ............ *G01N 23/04* (2013.01); *A61B 5/1075* (2013.01); *A61B 6/58* (2013.01); *A61B 6/582* (2013.01);
(Continued)

(58) Field of Classification Search
CPC .. G01N 23/04; G01N 2223/303; G01T 7/005; A61B 5/1075; A61B 6/58; A61B 6/582; A61B 6/585; G21K 1/02; G21K 2201/06
See application file for complete search history.

(56) References Cited

U.S. PATENT DOCUMENTS 3,206,604 A * 9/1965 Burchell ................. G21K 1/04
                                                   378/153
3,543,027 A * 11/1970 Nickless .............. G01N 23/083
                                                   250/363.01
(Continued)

FOREIGN PATENT DOCUMENTS

CN    101382504 A    3/2009
CN    101571496 A    11/2009
(Continued)

*Primary Examiner* — David P Porta
*Assistant Examiner* — Djura Malevic
(74) *Attorney, Agent, or Firm* — Kilpatrick Townsend & Stockton, LLP

(57) ABSTRACT

The present disclosure provides a ray calibration device and a working method thereof, and a radiation imaging system and a working method thereof, and belongs to the field of radiation imaging technology. The present disclosure can solve the problems that the existing calibration devices have low calibration efficiency and require relatively large spaces. The ray calibration device of the present disclosure includes a driving part, a cam part and a calibration part, wherein the calibration part is located below the cam part; the driving part is adapted to drive the cam part to rotate; and the cam part is adapted to exert a force on the calibration part to enable the calibration part to move into a ray area downwards.

18 Claims, 4 Drawing Sheets

(51) Int. Cl.
*A61B 5/107* (2006.01)
*A61B 6/00* (2006.01)
*G21K 1/06* (2006.01)

(52) U.S. Cl.
CPC ........ *A61B 6/585* (2013.01); *G01N 2223/303* (2013.01); *G01T 7/005* (2013.01); *G21K 1/06* (2013.01); *G21K 2201/06* (2013.01)

(56) References Cited

U.S. PATENT DOCUMENTS

| | | | | |
|---|---|---|---|---|
| 3,565,218 A * | 2/1971 | Kurt | F16D 57/04 | 188/290 |
| 3,631,249 A * | 12/1971 | Friede | A61B 6/06 | 378/157 |
| 3,894,234 A * | 7/1975 | Mauch | G01N 23/18 | 378/146 |
| 5,287,396 A * | 2/1994 | Stegehuis | A61B 6/06 | 378/151 |
| 5,561,290 A * | 10/1996 | Strobel | G01J 1/02 | 250/252.1 |
| 5,683,288 A * | 11/1997 | Kujawa | B24B 9/148 | 451/11 |
| 6,058,158 A * | 5/2000 | Eiler | B66C 19/007 | 378/197 |
| 6,242,743 B1 * | 6/2001 | DeVito | A61B 6/037 | 250/363.01 |
| 6,292,533 B1 * | 9/2001 | Swift | G01N 23/04 | 378/198 |
| 6,307,918 B1 * | 10/2001 | Toth | A61B 6/032 | 378/156 |
| 6,337,479 B1 * | 1/2002 | Kley | G11B 9/14 | 250/234 |
| 6,353,219 B1 * | 3/2002 | Kley | B82Y 10/00 | 250/234 |
| 6,763,635 B1 * | 7/2004 | Lowman | B60P 1/5433 | 378/198 |
| 6,920,197 B2 * | 7/2005 | Kang | G01N 23/04 | 378/198 |
| 7,327,830 B2 * | 2/2008 | Zhang | G01N 23/04 | 378/147 |
| 7,352,843 B2 * | 4/2008 | Hu | G01N 23/04 | 378/198 |
| 7,386,092 B2 * | 6/2008 | Kang | G01V 5/0008 | 378/197 |
| 7,881,424 B2 * | 2/2011 | Zhang | G01T 7/005 | 378/5 |
| 7,901,136 B2 * | 3/2011 | Harding | G01N 23/04 | 378/207 |
| 8,027,429 B2 * | 9/2011 | Hu | G01N 23/04 | 378/207 |
| 8,074,497 B2 * | 12/2011 | Sawa | G01N 3/42 | 73/81 |
| 9,366,610 B2 * | 6/2016 | Zhang | G01N 3/42 | |
| 9,406,411 B2 * | 8/2016 | Sayeh | G21K 1/04 | |
| 9,457,200 B2 * | 10/2016 | Matteo | F16C 19/54 | |
| 2007/0018117 A1 * | 1/2007 | Calderon | A61N 5/1048 | 250/492.1 |
| 2007/0019786 A1 * | 1/2007 | Zhang | G01N 23/04 | 378/57 |
| 2007/0110215 A1 * | 5/2007 | Hu | G01N 23/04 | 378/57 |
| 2008/0290265 A1 * | 11/2008 | Daly | G01J 5/62 | 250/252.1 |
| 2008/0310598 A1 * | 12/2008 | Zhang | G01T 7/005 | 378/207 |
| 2008/0315092 A1 * | 12/2008 | Kley | G01N 23/225 | 250/307 |
| 2009/0323894 A1 * | 12/2009 | Hu | G01N 23/04 | 378/53 |
| 2010/0111264 A1 * | 5/2010 | Henderson | A61N 5/10 | 378/197 |
| 2010/0124315 A1 * | 5/2010 | Harding | G01N 23/04 | 378/207 |
| 2010/0296631 A1 * | 11/2010 | Gillett | G21K 1/043 | 378/150 |
| 2012/0085909 A1 * | 4/2012 | Chen | G01K 11/006 | 250/338.1 |
| 2012/0203490 A1 * | 8/2012 | Sayeh | G21K 1/04 | 702/105 |
| 2013/0043390 A1 * | 2/2013 | De Ruyter | G01J 1/0295 | 250/338.1 |
| 2014/0076217 A1 * | 3/2014 | Liu | A01C 7/081 | 111/174 |
| 2014/0224003 A1 * | 8/2014 | Zhang | G01N 3/42 | 73/82 |
| 2014/0309959 A1 * | 10/2014 | Shen | G01N 33/241 | 702/100 |
| 2015/0126801 A1 * | 5/2015 | Matteo | A61N 5/1081 | 600/1 |
| 2016/0273323 A1 * | 9/2016 | Liu | F04B 47/028 | |
| 2017/0023697 A1 * | 1/2017 | Chen | G01V 5/0016 | |
| 2017/0184513 A1 * | 6/2017 | Chen | G01N 23/04 | |
| 2017/0269260 A1 * | 9/2017 | Chen | G01V 13/00 | |
| 2017/0343380 A1 * | 11/2017 | Liu | G01D 5/145 | |

FOREIGN PATENT DOCUMENTS

| | | |
|---|---|---|
| CN | 101614683 A | 12/2009 |
| CN | 102590890 A | 7/2012 |
| CN | 104483333 A | 4/2015 |
| CN | 204495742 U | 7/2015 |
| CN | 105675042 A | 6/2016 |
| JP | S5246152 U | 4/1977 |
| JP | S61193010 A | 8/1986 |
| JP | 2004184122 A | 7/2004 |
| KR | 20120118897 A | 10/2012 |

* cited by examiner

RAY CALIBRATION DEVICE AND OPERATING METHOD THEREOF, AND RADIATION IMAGING SYSTEM AND OPERATING METHOD THEREOF

FIELD OF THE DISCLOSURE

The present disclosure belongs to the field of radiation imaging technology, and specifically relates to a ray calibration device and an operating method thereof, and a radiation imaging system and an operating method thereof.

BACKGROUND OF THE DISCLOSURE

At present, in a ray imaging process, the performance of substance penetrated by rays needs to be calibrated to properly adjust the rays and image parameters to obtain a reasonable detection image. In the existing ray imaging technology, common ray calibration devices are divided into independent calibration devices and calibration devices integrated with accelerators (ray sources). The independent calibration device refers to that the calibration device is placed between the ray source and a detector, but this calibration device is generally relatively large in volume and weight, and is generally suitable for environments with relatively large spaces and sites. The calibration device integrated with the accelerator (the ray source) refers to that the calibration device and the accelerator (the ray source) are integrated into one part, so that the ray calibration device is compact in structure and is adaptive to the universal application of vehicle-mounted container detection systems and the calibration requirements of a variety of substances.

Among the calibration devices integrated with the accelerators (the ray sources), stage-by-stage scanning calibration devices and layer-by-layer superimposition calibration devices are common, but in the structures thereof, lead screws are needed to provide driving forces to cause pressing blocks to reciprocate. Due to such structures that cause the pressing blocks to reciprocate, the calibration efficiency is low, and the necessary spaces are relatively large, which is even unfavorable to the reduction of the volumes of the accelerators.

SUMMARY OF THE DISCLOSURE

In view of the problems that the existing calibration devices have low calibration efficiency and require relatively large spaces, the present disclosure provides a ray calibration device, which is compact in structure, small in space occupancy and high in calibration efficiency, and an operating method thereof, as well as a radiation imaging system and an operating method thereof.

The technical solution adopted to solve the technical problems in the present disclosure is a ray calibration device, including a driving part, a cam part and a calibration part, wherein the calibration part is located below the cam part;

the driving part is adapted to drive the cam part to rotate; and the cam part is adapted to exert a force on the calibration part to enable the calibration part to move into a ray area downwards.

The calibration part includes a calibration connecting unit and a calibration block, and the calibration block is arranged below the calibration connecting unit and is fixedly connected with the calibration connecting unit;

the cam part is adapted to exert the force on the calibration connecting unit to enable the calibration connecting unit to move downwards; and the calibration connecting unit is adapted to drive the calibration block to move into the ray area downwards.

The calibration part further includes a reset part, and the reset part is located below the calibration connecting unit and is connected with the calibration connecting unit; and the reset part is adapted to provide an upward restoring force for the calibration connecting unit, so that the calibration connecting unit drives the calibration block to return to an initial position.

The ray calibration device further includes a shielding part, the reset part includes a reset spring, one end of the reset spring is connected to the calibration connecting unit, and the other end of the reset spring is connected to the shielding part.

The ray calibration device further includes a guide slide rail, a slide block is arranged on the calibration connecting unit to engage with the guide slide rail, and the calibration connecting unit is slidably connected with the guide slide rail through the slide block; and the calibration connecting unit moves on the guide slide rail along the vertical direction through the slide block.

A roller is arranged on the calibration connecting unit; and the roller is adapted to rotate when the cam part exerts the force on the calibration connecting unit, in order to reduce the friction force between the calibration connecting unit and the cam part.

The cam part includes at least one sub-cam, each sub-cam includes a base circle section and a basic block, the basic block is located on the base circle section, a front end of the basic block is of a slope structure, and a rear end of the basic block is of a slope structure; and the basic block is adapted to press the calibration connecting unit downwards.

Each sub-cam further includes at least one additional block, the additional block is arranged on the base circle section and is located behind the basic block, the front end of the additional block is of an inverted slope structure for mating with the slope structure of the rear end of the basic block, and the rear end of the additional block is of a slope structure.

The structures of the basic blocks of the sub-cams are identical.

The structures of the additional blocks are identical.

There is at least one calibration part, and each calibration part corresponds to one sub-cam.

The cam part comprises a plurality of sub-cams, and the numbers of the additional blocks of the plurality of sub-cams are different.

The ray calibration device further includes a driving shaft, and the base circle section is sleeved on the driving shaft, so that the sub-cam is arranged on the driving shaft.

There is a plurality of sub-cams, and the plurality of sub-cams are sequentially arranged on the driving shaft.

The driving part includes a motor, a driving chain wheel, a driven chain wheel and a transmission chain, the transmission chain is sleeved on the driving chain wheel and the driven chain wheel, and the driven chain wheel is sleeved on the driving shaft; and the motor is adapted to drive the driving chain wheel to rotate and drive the driven chain wheel to rotate through the transmission chain, to cause the driving shaft to rotate.

As another technical solution, the present disclosure further provides a radiation imaging system, including a ray source and a ray calibration device, wherein the ray calibration device is any ray calibration device described above; and the ray source is adapted to emit rays to the calibration part, when the calibration part enters the ray area.

As another technical solution, the present disclosure further provides a working method of a ray calibration device, wherein the ray calibration device includes a driving part, a cam part and a calibration part, the calibration part being located below the cam part, the working method including:

driving, by the driving part, the cam part to rotate; and exerting, by the cam part, a force on the calibration part to enable the calibration part to move into a ray area downwards.

The working method of the ray calibration device further includes:

providing, by a reset part, an upward restoring force for a calibration connecting unit of the calibration part, so that the calibration connecting unit drives the calibration block to return to an initial position.

As another technical solution, the present disclosure further provides a working method of a radiation imaging system, wherein the radiation imaging system includes a ray source and a ray calibration device; and the ray calibration device includes a driving part, a cam part and a calibration part, the calibration part being located below the cam part, the working method including:

driving, by the driving part, the cam part to rotate;

exerting, by the cam part, a force on the calibration part to enable the calibration part to move into a ray area downwards;

emitting, by the ray source, rays to the calibration part, when the calibration part enters the ray area; and monitoring parameters of the radiation imaging system by the rays that penetrate through the calibration part.

In the ray calibration device and the working method thereof, as well as the radiation imaging system and the working method thereof of the present disclosure, the ray calibration device includes the driving part, the cam part and the calibration part, the driving part is adapted to drive the cam part to rotate, the cam part is adapted to exert the force on the calibration part to enable the calibration part to move into the ray area downwards. No lead screw is needed to provide a driving force, and accordingly a pressing block does not need to reciprocate, thus the calibration efficiency is improved; and in addition, the lead screw is linear, and no lead screw needs to be arranged, so that the structure of the ray calibration device can be more compact, and the space occupation area is reduced.

The ray calibration device of the present disclosure is suitable for the radiation imaging system in which the ray calibration device is integrated with an accelerator (the ray source).

Figure 1:
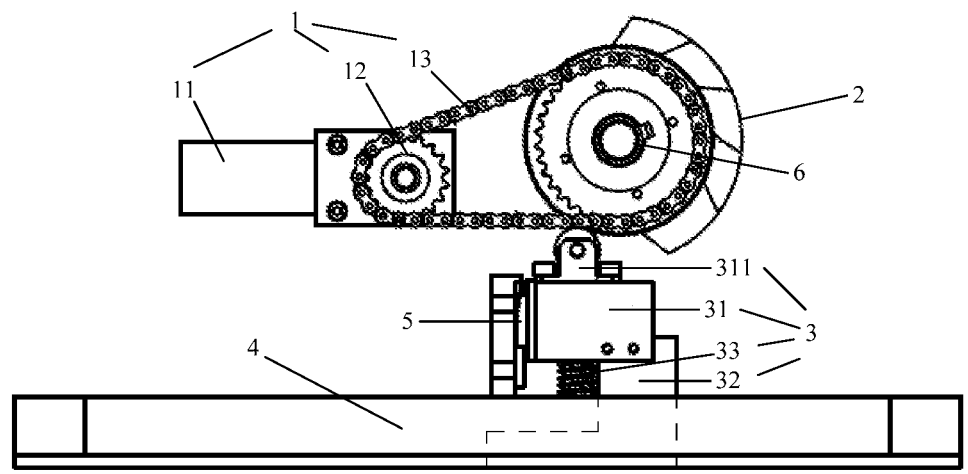
FIG. 1 is a schematic structural drawing of a ray calibration device in a first embodiment of the present disclosure.

wherein reference signs are as follows: 1. driving part; 11. motor; 12. driving chain wheel; 13. transmission chain; 14. driven chain wheel; 2. cam part; 21. sub-cam; 211. base circle section; 212. additional block; 213. basic block; 3. calibration part; 31. calibration connecting unit; 311. roller; 32. calibration block; 33. reset part; 4. shielding part; 5. guide slide rail; 6. driving shaft; 100. ray calibration device; and 200. ray source.

DETAILED DESCRIPTION OF THE EMBODIMENTS

In order that those skilled in the art better understand the technical solutions of the present disclosure, the present disclosure will be further described below in detail in combination with the accompany drawings and specific embodiments.

First Embodiment

Referring to FIGS. 1 to 5, the embodiment provides a ray calibration device, including a driving part 1, a cam part 2 and a calibration part 3, wherein the calibration part 3 is located below the cam part 2; the driving part 1 is adapted to drive the cam part 2 to rotate; and the cam part 2 is adapted to exert a force on the calibration part 3 to enable the calibration part 3 to move into a ray area downwards.

Preferably, the calibration part 3 includes a calibration connecting unit 31 and a calibration block 32, and the calibration block 32 is arranged below the calibration connecting unit 31 and is fixedly connected with the calibration connecting unit 31.

It can be seen from FIG. 1 that the calibration connecting unit 31 is arranged on one side close to the cam part 2 above the calibration block 32. Of course, the calibration connecting unit 31 and the calibration block 32 can be two separate structures, and can also be an integral structure, namely being integrally formed, as long as the calibration connecting unit 31 and the calibration block 32 can fix to each other.

The cam part 2 is adapted to exert the force on the calibration connecting unit 31 to enable the calibration connecting unit 31 to move downwards; and the calibration connecting unit 31 is adapted to drive the calibration block 32 to move into the ray area downwards.

Since the calibration connecting unit 31 is arranged above the calibration block 32, and the force exerted by the cam part 2 acts on the calibration connecting unit 31 earlier than the calibration block 32, the calibration connecting unit 31 moves downwards earlier due to the force exerted by the cam part 2. As the calibration connecting unit 31 is fixedly connected with the calibration block 32, the calibration connecting unit 31 moves downwards and drives the calibration block 32 to move also downwards under the action of the force, so as to enter the ray area.

Preferably, the calibration part 3 further includes a reset part 33, and the reset part 33 is located below the calibration connecting unit 31 and is connected with the calibration connecting unit 31. The reset part 33 is adapted to provide an upward restoring force for the calibration connecting unit 31, so that the calibration connecting unit 31 drives the calibration block 32 to return to an initial position. The initial position herein refer to a position in which the calibration block 32 is away from the ray area and is not penetrated by the rays.

Preferably, the ray calibration device further includes a shielding part 4. The reset part 33 includes a reset spring. One end of the reset spring is connected to the calibration connecting unit 31, and the other end of the reset spring is connected to the shielding part 4. The reason why the reset spring is selected is that the reset spring is easy to compress and stretch and can automatically deform in response to the exertion and disappearance of the acting force, in order to provide the restoring force. Of course, the reset part 33 is not limited to the reset spring and can also adopt other structure, as long as the effect of providing the restoring force can be achieved, and this will not be described redundantly herein.

Preferably, a roller 311 is arranged on the calibration connecting unit 31; and the roller 311 is adapted to rotate when the cam part 2 exerts the force on the calibration connecting unit 31, in order to reduce the friction force between the calibration connecting unit 31 and the cam part 2.

Figure 2:
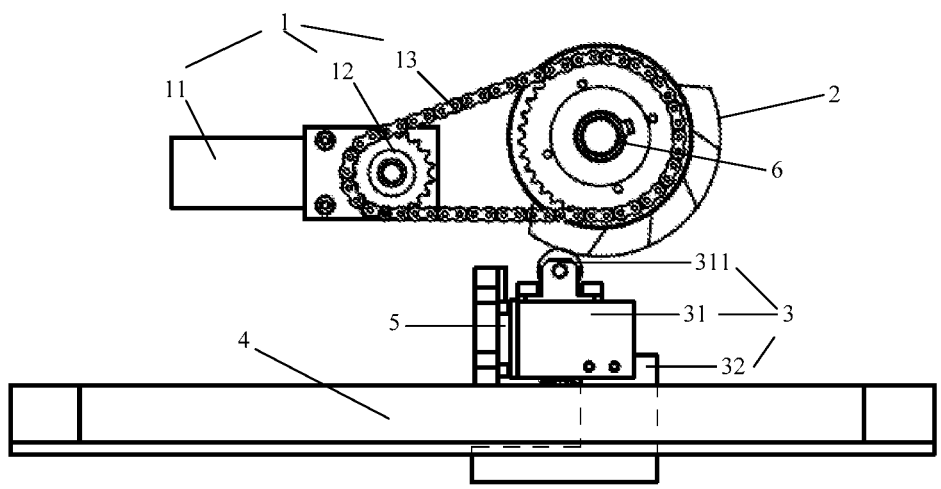
FIG. 2 is a schematic drawing of a working state of the ray calibration device in FIG. 1.

Referring to FIGS. 1 and 2, FIG. 1 is a schematic drawing of a working state of the ray calibration device, and FIG. 2 is a schematic drawing of another working state of the ray calibration device. When the ray calibration device works, the cam part 2 rotates clockwise under the drive of the driving part 1 and rotates from the position in FIG. 1 to the position in FIG. 2. At this time, the cam part 2 is in contact with the roller 311 and exerts the force on the same to drive the calibration part 3 to move downwards, so the calibration block 32 moves downwards, and a section (that is the area exposed below the shielding part 4 in FIG. 2) of the calibration block 32 enters the ray area, so that the rays penetrate through the section entering the ray area of the calibration block 32. At this time, the reset part 33 deforms and is compressed. The driving part 1 continuously rotates clockwise to drive the cam part 2 to rotate until the tail end (one end away from the roller 311 in FIG. 1) of the cam part 2 passes by the roller 311. At this time, the cam part 2 does not exert the force on the calibration part 3 anymore, the reset part 33 recovers its initial shape without force. As the reset part 33 recovers its initial shape, it provides the upward restoring force for the calibration connecting unit 31, so that the calibration connecting unit 31 drives the calibration block 32 to return to an initial position, namely the position in FIG. 1. That is to say, when the roller 311 is not stressed by the force of the cam part 2 anymore, the cam part 2 continuously rotates clockwise until rotating to the position in FIG. 1.

Preferably, the ray calibration device further includes a guide slide rail 5, a slide block is arranged on the calibration connecting unit 31 to engage with the guide slide rail 5, and the calibration connecting unit 31 is slidably connected with the guide slide rail 5 through the slide block. The calibration connecting unit 31 is adapted to move on the guide slide rail 5 along the vertical direction through the slide block.

The guide slide rail 5 is located on one side of the calibration part 3. The slide block (not shown in the figures) is arranged on the calibration connecting unit 31 to engage with the guide slide rail 5. The calibration connecting unit 31 is slidably connected with the guide slide rail 5 through the slide block. Of course, a rail identical as the guide slide rail 5 can also be arranged on the calibration connecting unit 31, and one or more balls are arranged between the guide slide rail 5 and the rail on the calibration connecting unit 31, thus the calibration connecting unit 31 can be slidably connected with the guide slide rail 5 through the balls. Sliding connection of the calibration connecting unit 31 and the guide slide rail 5 can be achieved in a variety of manners, as long as it can ensure the calibration connecting unit 31 moves on the guide slide rail 5 along the vertical direction through the slide block, and this will not be described redundantly herein.

Figure 3:
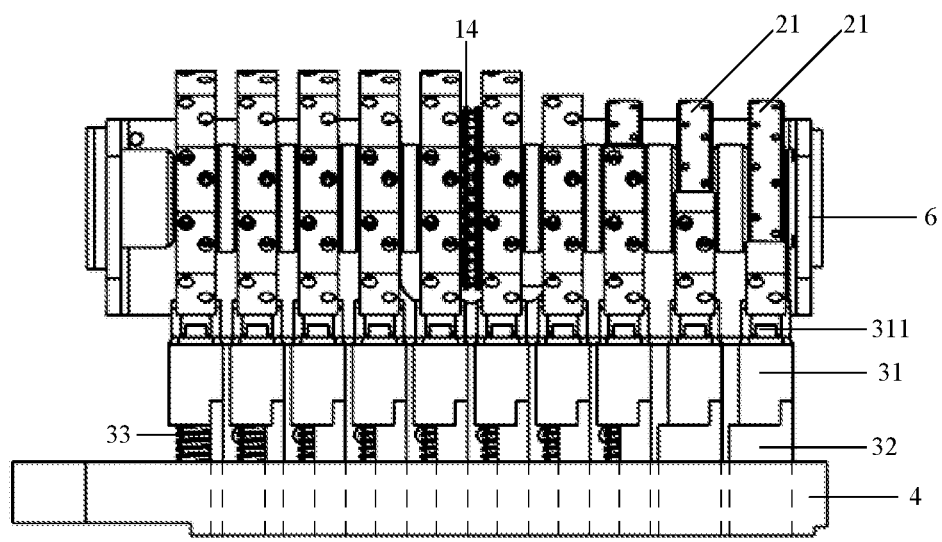
FIG. 3 is a front view of a cam part in FIG. 1.
Figure 4:
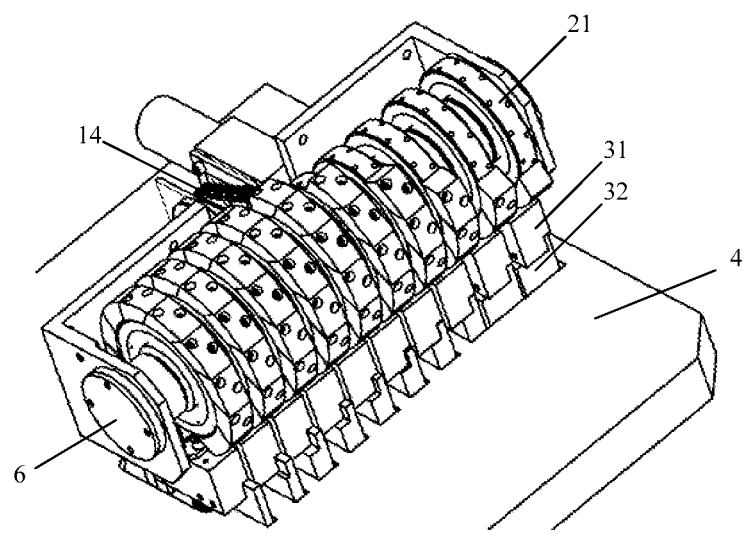
FIG. 4 is a side view of the cam part in FIG. 1.
Figure 5:
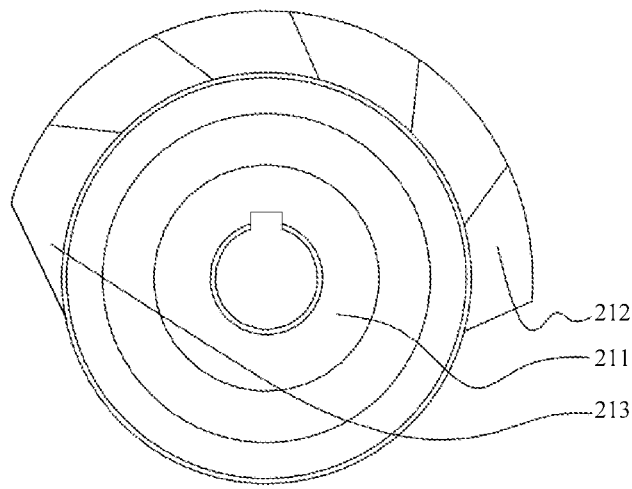
FIG. 5 is a schematic structural drawing of a sub-cam in FIG. 1.

As shown in FIG. 3 to 5, preferably, the cam part 2 includes at least one sub-cam 21, and each sub-cam 21 includes a base circle section 211 and a basic block 213. The basic block 213 is located on the base circle section 211. Front end of the basic block 213 is of a slope structure, and rear end of the basic block 213 is of a slope structure. The basic block 213 is adapted to press the calibration connecting unit 31 downwards.

Preferably, each sub-cam 21 further includes at least one additional block 212, and the additional block 212 is arranged on the base circle section 211 and is located behind the basic block 213. The front end of the additional block 212 is of an inverted slope structure for mating with the slope structure of the rear end of the basic block 213, and the rear end of the additional block 212 is of a slope structure. The additional block 212 is also adapted to press the calibration connecting unit 31 downwards.

The basic block 213 is arranged in each sub-cam 21, and the basic block 213 is located in front of the additional block 212, that is to say, the basic block 213 is in contact with the roller 311 earlier than the additional block 212. The front end of the basic block 213 is of the slope structure, in order to provide buffer, when the basic block 213 is in contact with the roller 311. It is conceivable if the front end of the basic block 213 is a right angle, even if the basic block is in contact with the roller 311, the roller 311 cannot "roll" from a vertical side of the basic block 213 to the surface of the basic block 213. As both ends of the basic block 213 are configured as the slope structures, the situation that the roller 311 cannot "roll" to the surface of the basic block 213 can be avoided, and buffer is provided for enabling the roller 311 to "roll" to the surface of the basic block 213. As the rear ends of the basic block 213 and the additional block 212 are configured as the slope structures, when the sub-cam 21 is provided with only one basic block 213, or when a plurality of additional blocks 212 are arranged behind the basic block 213, a buffer force can be provided for the roller 311 to leave the sub-cam 21.

Each sub-cam 21 includes a base circle section 211 and a basic block 213, and the basic block 213 is located on the base circle section 211, that is to say, the basic block 213 is fixedly arranged on the base circle section 211. However, the number of the additional blocks 212 arranged on the base circle section 211 is variable, namely the number of the additional blocks 212 can be increased or decreased according to actual conditions.

Preferably, the ray calibration device further includes a driving shaft 6, and the base circle section 211 is sleeved on the driving shaft 6, so that the sub-cam 21 is arranged on the driving shaft 6.

It should be noted that the cam part 2 is arranged on the driving part 1, and the driving part 1 drives the cam part 2 to rotate around axis of the driving shaft 6. The ray area is located below the shielding part 4. The rays are emitted by the ray source. The area passed by rays is the ray area. The ray direction is perpendicular to the shielding part 4, referring to FIG. 1 and FIG. 2, the rays perpendicularly emit from the interior of a paper surface to the exterior of the paper surface. The shielding part 4 is adapted to shield the calibration part 3, and is also used as a mounting frame of the ray calibration device for fixing various parts in the ray calibration device.

Preferably, when there is a plurality of sub-cams 21, the plurality of sub-cams 21 are sequentially arranged on the driving shaft 6. Referring to FIGS. 3 to 5, the cam part 2 includes at least one sub-cam 21, and the number of the sub-cams 21 can be adjusted according to actual demands. As shown in FIG. 3, 10 sub-cams 21 are sleeved on the driving shaft 6 side by side, the driving shaft 6 passes through the "hole" in the center of the base circle section 211 of each sub-cam 21, so as to sequentially arrange the plurality of sub-cams 21 together.

The number of the additional blocks 212 is related to the number of the sub-cams 21. Take 10 sub-cams 21 as an example. Referring to FIG. 3, starting from the left side in the figure, the sub-cams 21 are sequentially numbered and are marked as the first sub-cam, the second sub-cam, . . . the tenth sub-cam. The ray calibration device of the embodiment calibrates the rays in the layer-by-layer superimposition mode, therefore until the last calibration block enters the ray area, the calibration blocks that previously enter the ray area should keep a state within the ray area. Specifically, the number of the additional blocks on the first sub-cam is equal to the total number of the sub-cams minus 1, namely at least 9 additional blocks should be arranged on the first sub-cam, so as to guarantee that when the calibration block corresponding to the tenth sub-cam enters the ray area, the calibration block corresponding to the first sub-cam is still within the ray area. Similarly, at least 8 additional blocks should be arranged on the second sub-cam, so as to guarantee that when the calibration block corresponding to the tenth sub-cam enters the ray area, the calibration block corresponding to the second sub-cam is still within the ray area, and so on. On the tenth sub-cam is at least arranged the basic block 213 and no additional block 212. The number of the additional block(s) 212 needing to be arranged on each sub-cam can be obtained according to the above rule, and this will not be described redundantly herein. In FIG. 3, several additional blocks 212 close to the basic blocks 213 of the first sub-cam to the sixth sub-cam have passed by the corresponding calibration blocks, namely in the state that the calibration blocks are kept within the ray area, while the basic blocks 213 of the seventh sub-cam to the tenth sub-cam do not arrive at the top ends of the base circle sections 211, and thus the heights of the seventh sub-cam to the tenth sub-cam are lower than those of the first sub-cam to the sixth sub-cam.

Of course, if there are 10 sub-cams, but not all of the 10 sub-cams need to be used in actual operation, two solutions are available: one is that the unnecessary sub-cams are removed from the driving part 6; and the other is that the unnecessary sub-cams are not removed from the driving part 6, namely all of the 10 sub-cams are retained, the basic blocks 213 and the necessary number of additional blocks 212 are arranged only on the sub-cams needing to be used, the number of the additional blocks 212 can be obtained according to the above rule, and thus this will not be described redundantly herein.

The reason for such a configuration is that since the sub-cam 21 and the additional blocks 212 on the sub-cam 21 can be increased and decreased, the flexibility of use is improved. Preferably, the structures of the basic blocks 213 of the sub-cams 21 are identical, and the structures of the additional blocks 212 of the sub-cams 21 are identical. The structure herein includes shape, size and other parameters. The reason for such a configuration is that on the one hand, to guarantee that the heights of the sections entering the ray area of the calibration blocks 32 corresponding to each sub-cam 21 are unchanged, the thicknesses of the additional blocks 212 in the same sub-cam 21 should be identical, as shown in FIG. 5; and on the other hand, the types of the parts to be added are simplified, that is to say, the basic blocks 213 on all sub-cams 21 are identical, and the additional blocks 212 on all sub-cams 21 are identical, therefore only three types of parts need to be prepared in use, namely identical basic blocks 213, identical additional blocks 212 and one base circle section 211.

Preferably, there is at least one calibration part 3, and each calibration part 3 corresponds to one sub-cam 21. The number of the calibration parts 3 should be identical as the number of the sub-cams 21, that is to say, in the embodiment, if there are 10 sub-cams 21, 10 calibration parts 3 should be arranged correspondingly to the 10 sub-cams 21.

As mentioned above, when not all of the 10 sub-cams 21 need to be used in actual operation, no basic block 213 or additional block 212 is arranged in the sub-cams 21 that do not need to be used, in this way, as the sub-cam 21 is not provided with the basic block 213 or the additional block 212, the roller 311 of the calibration part 3 will be not pressed downwards, and thus the calibration block 32 of the calibration part 3 will not be pressed into the ray area.

Preferably, the driving part 1 includes a motor 11, a driving chain wheel 12, a driven chain wheel 14 and a transmission chain 13, and the transmission chain 13 is sleeved on the driving chain wheel 12 and the driven chain wheel 14. The motor 11 is adapted to drive the driving chain wheel 12 to rotate and drive the driven chain wheel 14 to rotate through the transmission chain 13, so as to cause the driving shaft 6 to rotate.

The motor 11 drives the driving chain wheel 12 to rotate and drives the driven chain wheel 14 to rotate through the transmission chain 13. As the driven chain wheel 14 is located on the driving shaft 6, the rotation of the driven chain wheel 14 can drive the driving shaft 6 to rotate, so as to drive the cam part 2 to rotate to exert the force on the calibration part 3.

The reason for such a configuration is that as this driving mode similar to a bicycle chain wheel is adopted, the arrangement of a lead screw device in the ray calibration device can be eliminated, so that the space occupation area can be effectively reduced, and the structure of the ray calibration device is more compact.

The ray calibration device in the embodiment includes the driving part 1, the cam part 2 and the calibration part 3. The driving part 1 is adapted to drive the cam part 2 to rotate, and the cam part 2 is adapted to exert the force on the calibration part 3 to enable the calibration part 3 to move into the ray area downwards. No lead screw is needed to provide a driving force, and accordingly a pressing block does not need to reciprocate, thus the calibration efficiency is improved. In addition, as the lead screw is linear, and no lead screw needs to be arranged, the structure of the ray calibration device can be more compact, and the space occupation area is reduced. Meanwhile, the structures of the basic blocks 213 on the sub-cams 21 are identical, and the structures of the additional blocks 212 are also identical, thereby not only guarantee that the heights of the sections entering the ray area of the calibration blocks 32 corresponding to each sub-cam 21 are unchanged, but also simplify the types of the parts to be added. The basic blocks 213 on all sub-cams 21 are identical, and the additional blocks 212 on all sub-cams 21 are identical, therefore only three types of parts need to be prepared in use, namely identical basic blocks 213, identical additional blocks 212 and one base circle section 211.

Second Embodiment

Figure 6:
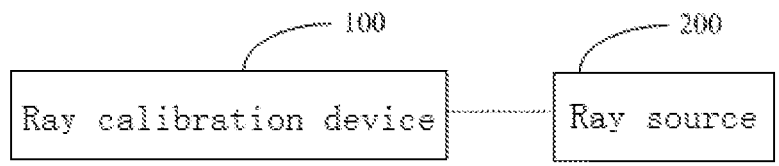
FIG. 6 is a schematic structural drawing of a radiation imaging system in a second embodiment of the present disclosure.

Referring to FIG. 6, the embodiment provides a radiation imaging system, including a ray source 200 and a ray calibration device 100, wherein the ray calibration device 100 is the ray calibration device in the first embodiment; and the ray source 200 is adapted to emit rays to the calibration part 3, when the calibration part 3 enters the ray area.

The radiation imaging system in the embodiment includes the ray source and the ray calibration device. The ray calibration device includes the driving part, the cam part and the calibration part. The driving part is adapted to drive the cam part to rotate, and the cam part is adapted to exert the force to the calibration part to enable the calibration part to move into the ray area downwards. No lead screw is needed to provide a driving force, and accordingly a pressing block does not need to reciprocate, thus the calibration efficiency is improved. In addition, as the lead screw is linear, and no lead screw needs to be arranged, the structure of the ray calibration device can be more compact, accordingly, the integral structure of the radiation imaging system is more compact, and the space occupation area is reduced. Meanwhile, the structures of the basic blocks 213 on the sub-cams 21 are identical, and the structures of the additional blocks 212 are identical, thereby not only guarantee that the heights of the sections entering the ray area of the calibration blocks 32 corresponding to each sub-cam 21 are unchanged, but also simplify the types of the parts to be added. The basic blocks 213 on all sub-cams 21 are identical, and the additional blocks 212 on all sub-cams 21 are identical, therefore only three types of parts need to be prepared in use, namely identical basic blocks 213, identical additional blocks 212 and one base circle section 211.

Third Embodiment

Figure 7:
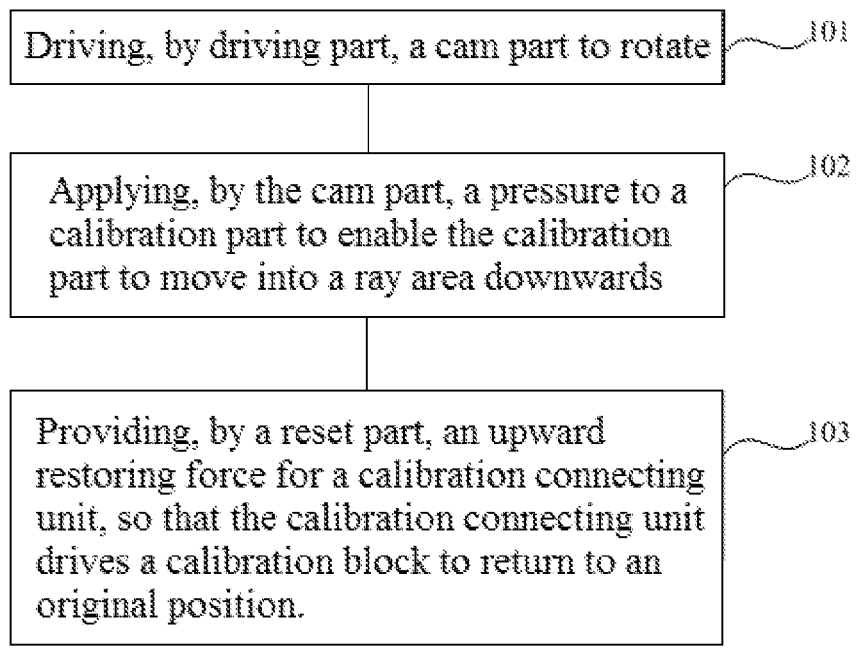
FIG. 7 is a schematic flow diagram of a working method of a ray calibration device in a third embodiment of the present disclosure.

Referring to FIG. 7, the embodiment provides a working method of a ray calibration device, wherein the ray calibration device 100 includes a driving part 1, a cam part 2 and a calibration part 3, the calibration part 3 being located below the cam part 2, the working method including:

step 101, the driving part 1 drives the cam part 2 to rotate.

Specifically, the motor 11 drives the driving chain wheel 12 to rotate and drives the driven chain wheel 14 to rotate through the transmission chain 13, and as the driven chain wheel 14 is located on the driving shaft 6, the rotation of the driven chain wheel 14 can cause the driving shaft 6 to rotate, so as to drive the cam part 2 to rotate.

Step 102, the cam part 2 exerts a force on the calibration part 3 to enable the calibration part 3 to move into a ray area downwards.

Step 103, the reset part 33 provides an upward restoring force for the calibration connecting unit 31, so that the calibration connecting unit 31 drives the calibration block 32 to return to an initial position.

Specifically, referring to FIGS. 1 and 2, the entire operating method can be understood as follows: When the ray calibration device works, the cam part 2 rotates from the position in FIG. 1 to the position in FIG. 2 under the drive of the driving part 1. At this time, the cam part 2 is in contact with the roller 311 and exerts the force on the same to cause the calibration part 3 to move downwards, and the calibration block 32 moves downwards, so that a section (that is the area exposed below the shielding part 4 in FIG. 2) of the calibration block 32 enters the ray area, then the rays penetrate through the section entering the ray area of the calibration block 32. At this time, the reset part 3 deforms and is compressed. The driving part 1 continuously rotates to drive the cam part 2 to rotate until the tail end of the cam part 2 passes by the roller 311. At this time, the cam part 2 does not exert the force on the calibration part 3 anymore, and the reset part 33 recovers its initial shape without force. As the reset part 33 recovers its initial shape, it provides the upward restoring force for the calibration connecting unit 31, so that the calibration connecting unit 31 drives the calibration block 32 to return to the initial position, namely the position in FIG. 1, and the current calibration is completed.

The working method of the ray calibration device provided by the embodiment can be applied to the calibration work of the ray calibration device in the first embodiment, reference can be made to the first embodiment for detailed description, and this will not be described redundantly herein.

According to the working method of the ray calibration device provided by the embodiment, the driving part 1 drives the cam part 2 to rotate, so that the cam part 2 exerts the force on the calibration part 3 to enable the calibration part 3 to move into the ray area downwards. After the force disappears, the reset part 33 provides the upward restoring force for the calibration connecting unit 31, so that the calibration connecting unit 31 drives the calibration block 32 to return to the initial position. In the method, no lead screw is needed to provide a driving force, and accordingly a pressing block does not need to reciprocate, thus the calibration efficiency is improved. The cam part 2 is only controlled by the driving part 1 to rotate, so the operation method is simpler and more reliable, and the operation cost is low.

Fourth Embodiment

Figure 8:
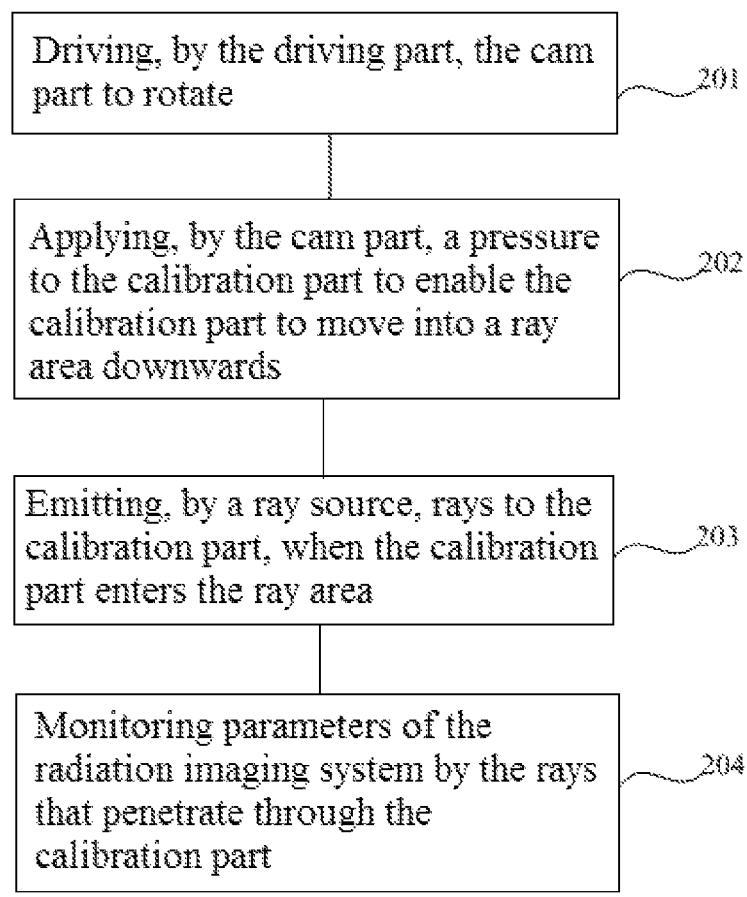
FIG. 8 is a schematic flow diagram of a working method of a ray calibration device in a fourth embodiment of the present disclosure.

Referring to FIG. 8, the embodiment provides a working method of a radiation imaging system, wherein the radiation imaging system includes a ray source 200 and a ray calibration device 100; and the ray calibration device 100 includes a driving part 1, a cam part 2 and a calibration part 3, the calibration part 3 being located below the cam part 2, the working method including:

Step 201, the driving part 1 drives the cam part 2 to rotate.

Step 202, the cam part 2 exerts a force on the calibration part 3 to enable the calibration part 3 to move into a ray area downwards.

Step 203, the ray source 200 emits rays to the calibration part 3, when the calibration part 3 enters the ray area.

With respect to the specific methods of the above steps, reference can be made to the third embodiment, and this will not be described herein in detail.

Step 204, parameters of the radiation imaging system are monitored by the rays that penetrate through the calibration part 3.

After penetrating through the calibration part 3, the rays will form an image in the radiation imaging system. The parameters of the radiation imaging system can be monitored according to the definition of the image, for example, if the image is unclear, a thinner calibration part 3 or the like can be selected and adjustment can be made according to actual conditions.

The working method of the radiation imaging system provided by the embodiment can be applied to the calibration work of the radiation imaging system in the second embodiment, reference can be made to the second embodiment for detailed description, and this will not be described redundantly herein.

According to the working method of the radiation imaging system provided by the embodiment, the parameters of the radiation imaging system can be monitored by the rays that penetrate through the calibration part 3, so that the operation method is simpler and more reliable, and the operation cost is low.

It can be understood that the above embodiments are merely exemplary embodiments adopted for illustrating the principle of the present disclosure, but the present disclosure is not limited hereto. Those of ordinary skill in the art can make a variety of modifications and improvements without departing from the spirit and the essence of the present disclosure, and these modifications and improvements shall all fall into the protection scope of the present disclosure.

The invention claimed is:

1. A ray calibration device, comprising a driving part, a cam part, a driving shaft and a calibration part,
wherein the calibration part is located below the cam part;
the driving part is adapted to drive the cam part to rotate around axis of the driving shaft; and
the cam part is adapted to exert a force on the calibration part to enable the calibration part to move into a ray area downwards.

2. The ray calibration device of claim 1, wherein the calibration part comprises a calibration connecting unit and a calibration block, and the calibration block is arranged below the calibration connecting unit and is fixedly connected with the calibration connecting unit;
the cam part is adapted to exert the force on the calibration connecting unit to enable the calibration connecting unit to move downwards; and
the calibration connecting unit is adapted to drive the calibration block to move into the ray area downwards.

3. The ray calibration device of claim 2, wherein the calibration part further comprises a reset part, and the reset part is located below the calibration connecting unit and is connected with the calibration connecting unit; and
the reset part is adapted to provide an upward restoring force for the calibration connecting unit, so that the calibration connecting unit drives the calibration block to return to an initial position.

4. The ray calibration device of claim 3, wherein the ray calibration device further comprises a shielding part, the reset part comprises a reset spring, one end of the reset spring is connected to the calibration connecting unit, and the other end of the reset spring is connected to the shielding part.

5. The ray calibration device of claim 2, further comprising a guide slide rail, a slide block is arranged on the calibration connecting unit to engage with the guide slide rail, and the calibration connecting unit is slidably connected with the guide slide rail through the slide block; and
the calibration connecting unit moves on the guide slide rail along the vertical direction through the slide block.

6. The ray calibration device of claim 2, wherein a roller is arranged on the calibration connecting unit; and
the roller is adapted to rotate when the cam part exerts the force to the calibration connecting unit, in order to reduce the friction force between the calibration connecting unit and the cam part.

7. The ray calibration device of claim 1, wherein the cam part comprises at least one sub-cam, each sub-cam comprises a base circle section and a basic block, the basic block is located on the base circle section, a front end of the basic block is of a slope structure, and a rear end of the basic block is of a slope structure; and
the basic block is adapted to press the calibration connecting unit downwards.

8. The ray calibration device of claim 7, wherein each sub-cam further comprises at least one additional block, the additional block is arranged on the base circle section and is located behind the basic block, the front end of the additional block is of an inverted slope structure for mating with the slope structure of the rear end of the basic block, and the rear end of the additional block is of a slope structure.

9. The ray calibration device of claim 7, wherein the structures of the basic blocks of the sub-cams are identical.

10. The ray calibration device of claim 8, wherein the structures of the additional blocks of the sub-cams are identical.

11. The ray calibration device of claim 1, wherein the cam part comprises at least one sub-cam, there is at least one calibration part, and each calibration part corresponds to one sub-cam.

12. The ray calibration device of claim 8, wherein the cam part comprises a plurality of sub-cams, and the numbers of the additional blocks of the plurality of sub-cams are different.

13. The ray calibration device of claim 7, wherein the base circle section is sleeved on the driving shaft, so that the sub-cam is arranged on the driving shaft.

14. The ray calibration device of claim 13, wherein the driving part comprises a motor, a driving chain wheel, a driven chain wheel and a transmission chain, the transmission chain is sleeved on the driving chain wheel and the driven chain wheel, and the driven chain wheel is sleeved on the driving shaft; and
the motor is adapted to drive the driving chain wheel to rotate and drive the driven chain wheel to rotate through the transmission chain, to cause the driving shaft to rotate.

15. A radiation imaging system, comprising a ray source and a ray calibration device, wherein the ray calibration device is the ray calibration device of any one of claim 1; and
the ray source is adapted to emit rays to the calibration part when the calibration part enters the ray area.

16. A working method of a ray calibration device, wherein the ray calibration device comprises a driving part, a cam part, a driving shaft, and a calibration part, the calibration part being located below the cam part, the working method comprising:
driving, by the driving part, the cam part to rotate around axis of the driving shaft; and
exerting, by the cam part, a force to the calibration part to enable the calibration part to move into a ray area downwards.

17. The working method of the ray calibration device of claim 16, further comprising:
providing, by a reset part, an upward restoring force for a calibration connecting unit of the calibration part, so that the calibration connecting unit drives a calibration block to return to an initial position.

18. A working method of a radiation imaging system, wherein the radiation imaging system comprises a ray source and a ray calibration device; the ray calibration device comprises a driving part, a cam part, a driving shaft and a calibration part, the calibration part being located below the cam part, the working method comprising:

driving, by the driving part, the cam part to rotate around axis of the driving shaft;
exerting, by the cam part, a force to the calibration part to enable the calibration part to move into a ray area downwards;
emitting, by the ray source, rays to the calibration part, when the calibration part enters the ray area; and
monitoring parameters of the radiation imaging system by the rays that penetrate through the calibration part.

* * * * *